(12) United States Patent
Bosch et al.

(10) Patent No.: US 8,258,132 B2
(45) Date of Patent: Sep. 4, 2012

(54) PHARMACEUTICAL COMPOSITION OF A TACHYKININ RECEPTOR ANTAGONIST

(75) Inventors: H. William Bosch, Bryn Mawr, PA (US); Elaine Liversidge, West Chester, PA (US); Suhas D. Shelukar, Lansdale, PA (US); Karen C. Thompson, Lansdale, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 1752 days.

(21) Appl. No.: 10/317,948

(22) Filed: Dec. 9, 2002

(65) Prior Publication Data

US 2004/0214746 A1   Oct. 28, 2004

Related U.S. Application Data

(60) Provisional application No. 60/340,040, filed on Dec. 10, 2001.

(51) Int. Cl.
*A61K 9/14* (2006.01)
*A61K 9/00* (2006.01)
*A61K 31/41* (2006.01)
*A61K 31/535* (2006.01)

(52) U.S. Cl. ....... 514/231.5; 424/46; 424/489; 514/383; 514/384

(58) Field of Classification Search .................. 424/489, 424/466, 464, 434, 44, 46; 514/535, 231.5, 514/383, 384
See application file for complete search history.

(56) References Cited

U.S. PATENT DOCUMENTS

| | | | |
|---|---|---|---|
| 5,145,684 A | 9/1992 | Liversidge et al. | |
| 5,399,363 A | 3/1995 | Liversidge et al. | |
| 5,552,160 A | 9/1996 | Liversidge et al. | |
| 5,573,783 A * | 11/1996 | Desieno et al. | 424/490 |
| 5,591,456 A | 1/1997 | Franson et al. | |
| 5,718,919 A | 2/1998 | Ruddy et al. | |
| 5,719,147 A | 2/1998 | Dorn et al. | |
| 5,998,435 A | 12/1999 | Horwell et al. | |
| 6,045,829 A | 4/2000 | Liversidge et al. | |
| 6,068,858 A * | 5/2000 | Liversidge et al. | 424/489 |
| 6,096,742 A | 8/2000 | Crocker et al. | |
| 6,165,506 A | 12/2000 | Jain et al. | |
| 6,235,735 B1 | 5/2001 | Dorn et al. | |
| 6,267,989 B1 | 7/2001 | Liversidge et al. | |
| 6,375,986 B1 * | 4/2002 | Ryde et al. | 424/489 |

FOREIGN PATENT DOCUMENTS

| | | |
|---|---|---|
| EP | 1000615 | 5/2000 |
| WO | 00/10545 | 3/2000 |

OTHER PUBLICATIONS

Liversidge et al., Particle size reduction for improvement of oral bioavailability of hydrophobic drugs: I. Absolute oral bioavailability of nanocrystalline danazol in beagle dogs; International Journal of Pharmaceutics 125, 91-97 (1995).*
Online Physician's Desk Reference, http://www.thomsonhc.com/predl/librarian/ND_T/PDRel/ND_CP/Pdr/DocumentId/52401-accessed on Aug. 23, 2008.*
Otsuka et al. Colloids and Surfaces B: Biointerfaces, 2000, vol. 17, pp. 145-152.*
Handbook of Pharmaceutical Excipients, "Hydroxypropyl Cellulose," American Pharmaceutical Association: Washington, D.C., 1986, pp. 134-135.*
Nisso HPC (Hydroxypropyl Cellulose) product brochure, accessed online on Apr. 15, 2010 at www.mmjp.or.jp/nisso-iyaku/pdf/hpc-brochure.pdf.*
Handbook of Pharmaceutical Controlled Release Technology, Donald L. Wise, editor, Marcell Dekker, Inc.: New York, 2000, pp. 347.*
Muller et al. "Nanosuspensions as particulate drug formulations in therapy: Rationale for development and what we can expect for the future," Advanced Drug Delivery Reviews, 2002, vol. 47, pp. 3-19.*
Olver et al. "Nanomedicines in the treatment of emesis during chemotherapy: focus on aprepitant," International Journal of Nanomedicine, 2007, 2(1), pp. 13-18.*
Hafizi et al. "Neurokini-1 receptor antagonists as novel antidepressants: trials and tribulations," The British Journal of Psychiatry, 2007, 191, pp. 282-284.*
Keller, M. et al. "Lack of Efficacy of the Substance P (Neurokinin1 Receptor) Antagonist Aprepitant in the Treatment of Major Depressive Disorder," Biological Psychiatry 2006, 59, pp. 216-223.*
Yunhui Wu et al, "The Role of Biopharmaceutics in the Development of a Clinical Nanoparticle Formulation of MK-0869: A Beagle dog Model Predicts Improved Bioavailability and Diminished Food Effect on Absorption in Human", International Journal of Pharmaceutics, 285, p. 135-146,(2004).
F. Kesisoglou et al., "Nanosizing-Oral Formulation Development and Biopharmaceutical Evaluation", Advanced Drug Delivery Reviews, vol. 59, pp. 631-644, 2007.
Notice of opposition to a European patent, No. EP 1455756 by Teva Pharmaceutical Industries, Ltd. received at the EPO on Apr. 6, 2009, pp. 2-23.
Notice of opposition to a European patent, No. EP 1455756 by Hexal AG, received at the EPO on Apr. 6, 2009, pp. 1-25.
Communication of notices of opposition from EPO dated May 14, 2009. Reply of the Patent Proprietor to the notices of opposition dated Nov. 30, 2009.
Hale, JJ et al., J. Med. Chem. vol. 43, (2000), pp. 1234-1241, "Phosphorylated morpholine acetal human neurokinin-1 receptor antagonists as water soluble prodrugs".
Newby DE et al., Br. J. Clin. Pharmacol., vol. 48, (1999), pp. 336-344, "Substance P-induced vasodilatation is mediated by the neurokinin type I receptor but does not contribute to basal vascular tone in man".
Technical Information, MC 069 d (262), Aug. 1997 (MPM), BASF, Cremophor RH40, pp. 1-6, Aug. 1997.
Kibble, AH, Handbook of Pharmaceutical Excipients, Third Edition, 2000, pp. 244-248, "Hydroxypropyl Cellulose".

(Continued)

*Primary Examiner* — James H. Alstrum-Acevedo
(74) *Attorney, Agent, or Firm* — Yong Zhao; David A. Muthard; Nicole M. Beeler

(57) ABSTRACT

The present invention is directed to novel pharmaceutical compositions of the compound 2-(R)-(1-(R)-(3,5-bis(trifluoromethyl)phenyl)ethoxy)-3-(S)-(4-fluoro)phenyl-4-(3-(5-oxo-1H,4H-1,2,4-triazolo)methylmorpholine. The pharmaceutical compositions of this invention useful in the treatment or prevention of disorders such as psychiatric disorders including depression and anxiety, inflammatory diseases and emesis.

10 Claims, No Drawings

OTHER PUBLICATIONS

Gill Jennings & Every LLP letter, Aug. 16, 2010, Opposition by Teva Pharmaceutical Industries, "Opponent's submission under R116 EPC".

Hubbard, AT; Book—Dispersion, Characterization, Testing and Measurement; Surfactant Science Series; 1999, Chapter 2, pp. 17-18 and 37-41 "Particle Characterization".

Jamzad, S et al., AAPS Pharm Sci Tech., vol. 7, No. 2, pp. E1-E6 (2006), "Role of Surfactant and pH on Dissolution Properties of Fenofibrate and Glipizide—A Technical Note".

Buchan, G, Communication dated Aug. 26, 2010, "Written submissions—oral proceedings scheduled for Oct. 28, 2010".

Maiwald Patentanwalts GmbH, Letter dated Aug. 25, 2010, Opposition by Hexal AG.

European Patent Office, Opposition Division, "Interlocutory decision in opposition proceedings and minutes of oral proceedings", dated Mar. 12, 2010.

* cited by examiner

PHARMACEUTICAL COMPOSITION OF A TACHYKININ RECEPTOR ANTAGONIST

CROSS REFERENCE TO RELATED APPLICATIONS

This application claims priority under 35 U.S.C. §119(e) from Provisional Application No. 60/340,040, filed Dec. 10, 2001.

BACKGROUND OF THE INVENTION

Substance P is a naturally occurring undecapeptide belonging to the tachykinin family of peptides, the latter being so-named because of their prompt contractile action on extravascular smooth muscle tissue. The tachykinins are distinguished by a conserved carboxyl-terminal sequence. In addition to SP the known mammalian tachykinins include neurokinin A and neurokinin B. The current nomenclature designates the receptors for substance P, neurokinin A, and neurokinin B as neurokinin-1 (NK-1), neurokinin-2 (NK-2), and neurokinin-3 (NK-3), respectively.

Evidence has been reviewed for the usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Chrohn's disease, ocular injury and ocular inflammatory diseases, proliferative vitreoretinopathy, irritable bowel syndrome and disorders of bladder function including cystitis and bladder detruser hyperreflexia.

It has furthermore been suggested that tachykinin receptor antagonists have utility in the following disorders: anxiety, depression, dysthymic disorders, chronic obstructive airways disease, hypersensitivity disorders such as poison ivy, vasospastic diseases such as angina and Reynauld's disease, fibrosing and collagen diseases such as scleroderma and eosinophillic fascioliasis, reflex sympathetic dystrophy such as shoulder/hand syndrome, addiction disorders such as alcoholism, stress related somatic disorders, neuropathy, neuralgia, disorder related to immune enhancement or suppression such as systemic lupus erythmatosus, ophthalmic diseases such as conjunctivitis, vernal conjunctivitis, and the like, and cutaneous diseases such as contact dermatitis, atopic dermatitis, urticaria, and other eczematoid dermatitis.

Attempts have been made to provide antagonists for the receptors of substance P and other tachykinin peptides in order to more effectively treat the various disorders and diseases mentioned above. In particular, PCT Publication No. WO 94/00440, EPO Publication No. 0,577,394, PCT Publication No. WO 95/16679, U.S. Pat. No. 5,719,147 and U.S. Pat. No. 6,096,742 disclose certain morpholine and thiomorpholine compounds as substance P antagonists. In particular, the compound 2-(R)-(1-(R)-(3,5-bis(trifluoromethyl)-phenyl)ethoxy)-3-(S)-(4-fluoro)phenyl-4-(3-(5-oxo-1H,4H-1,2,4-triazolo)methylmorpholine is disclosed as the title compound of Example 75 of U.S. Pat. No. 5,719,147.

Nanoparticulate compositions, first described in U.S. Pat. No. 5,145,684, are particles consisting of a poorly soluble therapeutic or diagnostic agents having adsorbed onto the surface thereof a non-crosslinked surface stabilizer. This and later references do not describe nanoparticulate compositions comprising 2-(R)-(1-(R)-(3,5-bis(trifluoromethyl)phenyl) ethoxy)-3-(S)-(4-fluoro)phenyl-4-(3-(5-oxo-1H,4H-1,2,4-triazolo)methylmorpholine.

SUMMARY OF THE INVENTION

This invention is concerned with novel pharmaceutical compositions of the compound 2-(R)-(1-(R)-(3,5-bis(trifluoromethyl)-phenyl)ethoxy)-3-(S)-(4-fluoro)phenyl-4-(3-(5-oxo-1H,4H-1,2,4-triazolo)methylmorpholine. The pharmaceutical compositions of this invention useful in the treatment or prevention of disorders which benefit from the use of a tachykinin receptor antagonist, including central nervous system disorders such as psychiatric disorders including depression and anxiety, inflammatory diseases and emesis. These pharmaceutical compositions advantages over the other known pharmaceutical compositions of 2-(R)-(1-(R)-(3,5-bis(trifluoromethyl)-phenyl)ethoxy)-3-(S)-(4-fluoro) phenyl-4-(3-(5-oxo-1H,4H-1,2,4-triazolo)methyl-morpholine in terms of increased oral bioavailability.

DESCRIPTION OF THE INVENTION

The present invention is directed to novel pharmaceutical compositions of the compound 2-(R)-(1-(R)-(3,5-bis(trifluoromethyl)-phenyl)ethoxy)-3-(S)-(4-fluoro)phenyl-4-(3-(5-oxo-1H,4H-1,2,4-triazolo)methylmorpholine and the process for the preparation of these pharmaceutical compositions.

The compound 2-(R)-(1-(R)-(3,5-bis(trifluoromethyl) phenyl)ethoxy)-3-(S)-(4-fluoro)phenyl-4-(3-(5-oxo-1H,4H-1,2,4-triazolo)methylmorpholine has the structure:

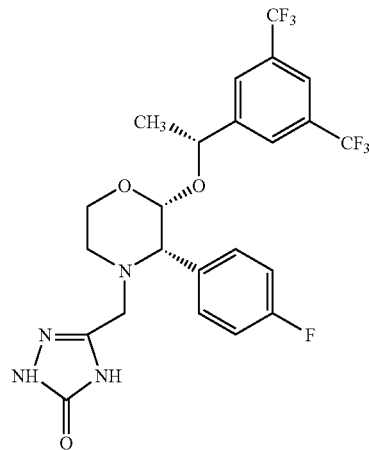

and is a tachykinin receptor antagonist useful in the treatment of disorders which benefit from the use of a tachykinin receptor antagonist, including central nervous system disorders such as psychiatric disorders including depression and anxiety, inflammatory diseases, pain or migraine, asthma, and emesis.

The present invention is directed to pharmaceutical compositions that employ nanoparticulate compositions of the compound 2-(R)-(1-(R)-(3,5-bis(trifluoro-methyl)phenyl) ethoxy)-3-(S)-(4-fluoro)phenyl-4-(3-(5-oxo-1H,4H-1,2,4-triazolo)-methylmorpholine. The nanoparticulate compositions comprise the compound 2-(R)-(1-(R)-(3,5-bis (trifluoromethyl)-phenyl)ethoxy)-3-(S)-(4-fluoro)phenyl-4-

(3-(5-oxo-1H,4H-1,2,4-triazolo)methylmorpholine and at least one surface stabilizer adsorbed to the surface of the compound.

Another aspect of the invention is directed to pharmaceutical compositions comprising a nanoparticulate composition of the compound 2-(R)-(1-(R)-(3,5-bis(trifluoromethyl)phenyl)ethoxy)-3-(S)-(4-fluoro)phenyl-4-(3-(5-oxo-1H,4H-1,2,4-triazolo)methylmorpholine. The pharmaceutical composition comprises the compound 2-(R)-(1-(R)-(3,5-bis(trifluoromethyl)phenyl)ethoxy)-3-(S)-(4-fluoro)phenyl-4-(3-(5-oxo-1H,4H-1,2,4-triazolo)methylmorpholine, at least one surface stabilizer adsorbed to the surface of the drug, and a pharmaceutically acceptable carrier, as well as any desired excipients.

Applicants have unexpectedly found that a suspension, dispersion or solid dosage formulation of 2-(R)-(1-(R)-(3,5-bis(trifluoromethyl)phenyl)ethoxy)-3-(S)-(4-fluoro)phenyl-4-(3-(5-oxo-1H,4H-1,2,4-triazolo)methylmorpholine, having a particle size of less than about 1000 nm, and a surface stabilizer (e.g., hydroxypropyl cellulose) substantially improves the bioavailability of the compound.

The present invention provides a nanoparticulate composition (i.e., "nanoparticles") comprising the compound 2-(R)-(1-(R)-(3,5-bis(trifluoromethyl)-phenyl)ethoxy)-3-(S)-(4-fluoro)phenyl-4-(3-(5-oxo-1H,4H-1,2,4-triazolo)methylmorpholine, or a pharmaceutically acceptable salt thereof, the compound having adsorbed on the surface thereof a surface stabilizer in an amount sufficient to maintain an effective average particle size of less than about 1000 nm, preferably, less than about 400 nm, more preferably, less than about 250 nm, and most preferably, less than about 100 nm. The compound having the surface stabilizer adsorbed on the surface thereof to maintain an effective average particle size of less than about 1000 nm (preferably, less than about 400 nm, more preferably, less than about 250 nm, and most preferably, less than about 100 nm) is also referred to herein as the active ingredient "nanoparticles" or "nanoparticulate drug particles."

In one embodiment of the invention is the nanoparticulate composition wherein the surface stabilizer is selected from HPC, HPMC, HPC-SL or HPC-L.

In another aspect of the invention, the nanoparticles have at least one additional surface stabilizer adsorbed to the surface of the active ingredient.

The present invention also provides a solid dose nanoparticulate composition comprising the instant nanoparticles.

The invention also provides a pharmaceutical dispersion comprising a liquid dispersion medium and the above-described nanoparticles dispersed therein. The terms "dispersion" or "suspension" are synonymous and used interchangeably herein and refer to a formulation in which the active ingredient nanoparticles remain suspended undissolved in a fluid such as water.

The present invention is further directed to processes for making a nanoparticulate composition of the compound 2-(R)-(1-(R)-(3,5-bis(trifluoromethyl)phenyl)ethoxy)-3-(S)-(4-fluoro)phenyl-4-(3-(5-oxo-1H,4H-1,2,4-triazolo)-methylmorpholine having at least one surface stabilizer adsorbed on the surface of the compound. Such processes comprise contacting the compound 2-(R)-(1-(R)-(3,5-bis(trifluoromethyl)phenyl)ethoxy)-3-(S)-(4-fluoro)phenyl-4-(3-(5-oxo-1H,4H-1,2,4-triazolo)methylmorpholine with at least one surface stabilizer for a time and under conditions sufficient to provide a nanoparticle/surface stabilizer composition. The surface stabilizers can be contacted with the compound either before, during, or after size reduction of the compound.

The present invention is further directed to methods of treatment comprising administering to a patient in need a therapeutically effective amount of a pharmaceutical composition according to the present invention.

The nanoparticulate compositions of the present invention comprise the compound 2-(R)-(1-(R)-(3,5-bis(trifluoromethyl)phenyl)ethoxy)-3-(S)-(4-fluoro)phenyl-4-(3-(5-oxo-1H,4H-1,2,4-triazolo)methylmorpholine having at least one surface stabilizer adsorbed on the surface thereof. The nanoparticulate compositions have an effective average particle size of less than about 2000 nm. Preferably, the effective average particle size is less than about 1500 nm, less than about 1000 nm, less than about 800 nm, less than about 600 nm, less than about 500 nm, less than about 400 nm, less than about 300 nm, less than about 250 nm, less than about 100 nm, or less than about 50 nm. Surface stabilizers useful herein physically adhere to the surface of the compound, but do not chemically react with the drug or itself. Individually adsorbed molecules of the surface stabilizer are essentially free of intermolecular cross-linkages.

The present invention also includes nanoparticulate compositions having at least one surface stabilizer adsorbed on the surface thereof, formulated into compositions together with one or more non-toxic physiologically acceptable carriers, adjuvants, or vehicles, collectively referred to as carriers. The compositions can be formulated for parenteral injection, oral administration in solid or liquid form, rectal or topical administration, aerosol administration, and the like.

The nanoparticles of the invention comprise the compound 2-(R)-(1-(R)-(3,5-bis(trifluoromethyl)phenyl)ethoxy)-3-(S)-(4-fluoro)phenyl-4-(3-(5-oxo-1H,4H-1,2,4-triazolo)methylmorpholine. The compound exists either as a discrete crystalline phase or as an amorphous phase. The crystalline phase differs from a non-crystalline or amorphous phase which results from precipitation techniques.

Useful surface stabilizers, which are known in the art and described for example in U.S. Pat. No. 5,145,684, are believed to include those which physically adhere to the surface of the active agent but do not chemically bond to or interact with the active agent. The surface stabilizer is adsorbed on the surface of the compound 2-(R)-(1-(R)-(3,5-bis(trifluoromethyl)phenyl)ethoxy)-3-(S)-(4-fluoro)phenyl-4-(3-(5-oxo-1H,4H-1,2,4-triazolo)methylmorpholine in an amount sufficient to maintain an effective average particle size of less than about 2000 nm for the active agent. Furthermore, the individually adsorbed molecules of the surface stabilizer are essentially free of intermolecular cross-linkages. Two or more surface stabilizers can be employed in the compositions and methods of the invention.

Suitable surface stabilizers can preferably be selected from known organic and inorganic pharmaceutical excipients. Such excipients include various polymers, low molecular weight oligomers, natural products, and surfactants. Preferred surface stabilizers include nonionic and ionic surfactants.

Representative examples of surface stabilizers include gelatin, casein, lecithin (phosphatides), dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available Tweens® such as e.g., Tween 20® and Tween 80® (ICI Speciality Chemicals)); polyethylene glycols (e.g., Carbowaxs 3550® and 934® (Union Carbide)), polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethyl-cellulose, hydroxypropylmethyl-cellulose phthalate, noncrystalline cellulose, magnesium aluminium silicate, triethanolamine, polyvinyl alcohol (PVA), polyvinylpyrrolidone (PVP), 4-(1,1,3,3-tetramethylbutyl)-phenol polymer with ethylene oxide and formaldehyde (also known as tyloxapol, superione, and triton), poloxamers (e.g., Pluronics F68® and F108®, which are block copolymers of ethylene oxide and propylene oxide); poloxamines (e.g., Tetronic 908®, also known as Poloxamine 908®, which is a tetrafunctional block copolymer derived from sequential addition of propylene oxide and ethylene oxide to ethylenediamine (BASF Wyandotte Corporation, Parsippany, N.J.)); Tetronic 1508® (T-1508) (BASF Wyandotte Corporation), dialkylesters of sodium sulfosuccinic acid (e.g., Aerosol OT®, which is a dioctyl ester of sodium sulfosuccinic acid (American Cyanamid)), dioctyl sodium sulfosuccinate (DOSS), docusate Sodium (Ashland Chem. Co., Columbus, Ohio); Duponol P®, which is a sodium lauryl sulfate (DuPont); Tritons X-200®, which is an alkyl aryl polyether sulfonate (Rohm and Haas); Crodestas F-110®, which is a mixture of sucrose stearate and sucrose distearate (Croda Inc.); p-isononylphenoxy-poly-(glycidol), also known as Olin-IOG® or Surfactant 10-G® (Olin Chemicals, Stamford, Conn.); Crodestas SL-40® (Croda, Inc.); and SA9OHCO, which is $C_{18}H_{37}CH_2(CON(CH_3)—CH_2(CHOH)_4(CH_2OH)_2$ (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methyl-glucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; and the like.

Most of these surface stabilizers are known pharmaceutical excipients and are described in detail in the *Handbook of Pharmaceutical Excipients*, published jointly by the American Pharmaceutical Association and The Pharmaceutical Society of Great Britain (The Pharmaceutical Press, 1986), specifically incorporated by reference. The surface stabilizers are commercially available and/or can be prepared by techniques known in the art.

The nanoparticles of the invention contain a discrete phase of an active ingredient with the surface stabilizer adsorbed on the surface thereof. It has been discovered that the surface stabilizer physically adheres to the active ingredient, but it does not chemically bond to or chemically react with the drug. Such chemical bonding or interaction would be undesirable as it could result in altering the function of the drug. The surface stabilizer is adsorbed on the surface of the active ingredient in an amount sufficient to maintain an effective average particle size of less than about 1000 nm, and more preferably, less than about 400 nm, and most preferably, less than about 250 nm. Furthermore, the individually adsorbed molecules of the surface stabilizer are essentially free of intermolecular cross-linkages.

In an aspect of the present invention the surface stabilizer is selected from hydroxypropyl cellulose (HPC), which is an ether of cellulose, HPC super low viscosity (HPC-SL), HPC-low viscosity (KPC-L), and hydroxypropyl methyl cellulose (HPMC). Preferred surface stabilizers include, but are not limited to hydroxypropyl cellulose (HPC), HPC-SL, HPC-L, methyl cellulose, hydroxyethyl cellulose, carboxymethyl cellulose sodium or hydroxypropyl methylcellulose (HPMC).

(see, e.g., Remington's at pp. 1304-1308). Preferably, HPC, HPC-SL, HPC-L or HPMC are used as surface stabilizers; HPC-SL is particularly preferred as the surface stabilizer.

The relative amount of the compound 2-(R)-(1-(R)-(3,5-bis(trifluoro-methyl)phenyl)ethoxy)-3-(S)-(4-fluoro)phenyl-4-(3-(5-oxo-1H,4H-1,2,4-triazolo)-methylmorpholine and one or more surface stabilizers can vary widely. The optimal amount of the surface stabilizers can depend, for example, upon hydrophilic lipophilic balance (HLB), melting point, and water solubility of the surface stabilizer, and the surface tension of water solutions of the stabilizer, etc.

In another embodiment of the invention, there is provided a method of preparing the above-described nanoparticulate drug particles. The method comprises dispersing an active ingredient in a liquid dispersion medium and applying mechanical means in the presence of grinding media to reduce the average particle size of the active ingredient to an effective average particle size of less than about 1000 nm, more preferably, less than about 400 nm, and most preferably, less than about 250 nm. The drug particles can be reduced in size in the presence of a surface stabilizer, or the drug particles can be contacted with a surface stabilizer after attrition.

In another embodiment of the invention, a method for preparing a nanoparticulate pharmaceutical composition in a tablet form is provided. In such a method, the nanoparticles are compressed into tablets. The tablets generally also comprise at least one pharmaceutically acceptable carrier.

Another embodiment of the invention is directed to nanoparticulate pharmaceutical composition wherein the dispersion of surface stabilizer and nanoparticulate compound 2-(R)-(1-(R)-(3,5-bis(trifluoromethyl)phenyl)ethoxy)-3-(S)-(4-fluoro)phenyl-4-(3-(5-oxo-1H,4H-1,2,4-triazolo)methylmorpholine has been spray dried or spray coated onto a solid support such as cellulose or sugar spheres or onto another pharmaceutical excipient.

More specifically illustrating the invention is a process for making a nanoparticulate composition comprising
(a) dispersing the compound 2-(R)-(1-(R)-(3,5-bis(trifluoro-methyl)phenyl)ethoxy)-3-(S)-(4-fluoro)phenyl-4-(3-(5-oxo-1H,4H-1,2,4-triazolo)methyl-morpholine in a liquid dispersion medium,
(b) wet grinding the compound in the presence of rigid grinding media having an average particle size of less than about 3 mm and a surface stabilizer to reduce the particle size of the active ingredient to an effective average particle size of less than about 1000 nm (preferably, less than about 400 nm, and more preferably, less than about 250 nm), and
(c) isolating the resultant nanoparticulate composition from the grinding media.

An embodiment of the invention is directed to a nanoparticulate composition prepared by such process.

Further exemplifying the invention is a process for making a nanoparticulate composition comprising:
(a) dispersing the compound 2-(R)-(1-(R)-(3,5-bis(trifluoro-methyl)phenyl)ethoxy)-3-(S)-(4-fluoro)phenyl-4-(3-(5-oxo-1H,4H-1,2,4-triazolo)methyl-morpholine in a liquid dispersion medium,
(b) wet grinding the compound in the presence of rigid grinding media having an average particle size of less than about 3 mm to form a dispersion medium,
(c) contacting the dispersion medium comprising the ground active ingredient with a surface stabilizer by mixing the surface stabilizer with the dispersion medium to form particles having an average effective particle size of less than about 1000 nm (preferably, less than about 400 nm, and more preferably, less than about 250 nm), and (d) isolating the resultant nanoparticulate composition from the grinding media.

An embodiment of the invention is directed to a nanoparticulate composition prepared by such process.

The present invention is also concerned with a process for the preparation of a pharmaceutical formulation of 2-(R)-(1-(R)-(3,5-bis(trifluoromethyl)-phenyl)ethoxy)-3-(S)-(4-fluoro)phenyl-4-(3-(5-oxo-1H,4H-1,2,4-triazolo)methylmorpholine which comprises:

preparing a nanoparticulate suspension of of 2-(R)-(1-(R)-(3,5-bis(trifluoromethyl)phenyl)ethoxy)-3-(S)-(4-fluoro)phenyl-4-(3-(5-oxo-1H,4H-1,2,4-triazolo)methylmorpholine and a surface stabilizer such as hydroxypropyl cellulose;

adding a redispersant aid such as sucrose;

spraycoating the suspension onto a solid support such as cellulose spheres to form coated spheres;

lubricated the coated spheres with a lubircant such as sodium lauryl sulfate;

optionally encapsulating the resultant product into hard gelatin capsules.

An embodiment of the invention is directed to a pharmaceutical composition prepared by such process.

Further illustrating the invention is a process for making a pharmaceutical dispersion which comprises mixing (suspending) the nanoparticulate composition described above in a liquid dispersion medium.

More specifically exemplifying the invention is a pharmaceutical dispersion made by mixing (suspending) the nanoparticulate composition in a liquid dispersion medium.

An additional example of the invention is a pharmaceutical formulation made by any of the processes described above.

As used herein, particle size is determined on the basis of the weight average particle size as measured by conventional particle size measuring techniques well known to those skilled in the art. Such techniques include, for example, sedimentation field flow fractionation, photon correlation spectroscopy light scattering, and disk centrifugation.

By "an effective average particle size of less than about 1000 nm" it is meant that at least 50% of the 2-(R)-(1-(R)-(3,5-bis(trifluoromethyl)phenyl)ethoxy)-3-(S)-(4-fluoro)phenyl-4-(3-(5-oxo-1H,4H-1,2,4-triazolo)methylmorpholine particles have an average particle size of less than about 1000 nm when measured by the above techniques. Preferably, at least 70% of the particles have an average particle size of less than the effective average, i.e., about 1000 nm, more preferably at least about 90% of the particles have an average particle size of less than the effective average. In preferred embodiments, the effective average particle size is less than about 800 nm, less than about 600 nm, less than about 500 nm, less than about 400 nm, less than about 300 nm, less than about 250 nm, less than about 100 nm, or less than about 50 nm.

The terms "dispersion" and "suspension" are synonymous and used interchangeably herein and refer to a formulation where the ingredient particles remain suspended undissolved in a fluid such as water.

The term "patient" or "subject" as used herein refers to an animal, preferably a mammal, most preferably a human (such as an adult, including an elderly adult such as an elderly man or an elderly woman), who has been the object of treatment, observation or experiment.

The term "therapeutically effective amount" as used herein means that amount of active compound or pharmaceutical agent that elicits the biological or medicinal response in a tissue, system, animal or human that is being sought by a researcher, veterinarian, medical doctor or other clinician, which includes alleviation of the symptoms of the disease being treated.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

Pharmaceutically acceptable salts can be prepared from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media such as ether, ethyl acetate, ethanol, isopropanol, or acetonitrile are preferred. Suitable salts are found, e.g. in Remington's Pharmaceutical Sciences, 17th ed., Mack Publishing Company, Easton, Pa., 1985, p. 1418.

Methods for preparing the compound 2-(R)-(1-(R)-(3,5-bis(trifluoro-methyl)phenyl)ethoxy)-3-(S)-(4-fluoro)phenyl-4-(3-(5-oxo-1H,4H-1,2,4-triazolo)-methylmorpholine are fully described e.g. in U.S. Pat. Nos. 5,719,147, 6,096,742, 6,255,545, 6,297,376, 6,350,915, 6,407,255, and 6,469,164.

With respect to pharmaceutical compositions of the compound 2-(R)-(1-(R)-(3,5-bis(trifluoromethyl)phenyl)ethoxy)-3-(S)-(4-fluoro)phenyl-4-(3-(5-oxo-1H,4H-1,2,4-triazolo)methylmorpholine disclosed in the art, the pharmaceutical compositions of the present invention exhibit unexpected properties, such as enhanced oral bioavailability or absorption and/or with respect to aqueous solubility, stability, ease of preparation and/or metabolism.

The pharmaceutical compositions of this invention may be used in the form of a pharmaceutical preparation, for example, in solid, semisolid or liquid form, which contains one or more of the compounds of the present invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of the disease.

In a class of the invention is the pharmaceutical dispersion wherein the liquid dispersion medium is selected from water, safflower oil, ethanol, t-butanol, hexane or glycol. Preferably, the liquid dispersion medium is water.

Pharmaceutical compositions according to the invention may also comprise one or more binding agents, filling agents, lubricating agents, suspending agents, sweeteners, flavoring agents, preservatives, buffers, wetting agents, disintegrants, effervescent agents, and other excipients. Such excipients are known in the art.

The surface stabilizer can also be used in conjunction with one or more other surface stabilizers. Suitable additional surface stabilizers can preferably be selected from known organic and inorganic pharmaceutical excipients. Such excipients include various polymers, low molecular weight oligomers, natural products and surfactants. Preferred additional surface stabilizers include nonionic and anionic surfactants. Representative examples of excipients include gelatin, casein, lecithin (phosphatides), gum acacia, cholesterol, tragacanth, stearic acid, benzalkonium chloride, calcium stearate, glyceryl monostearate, cetostearl alcohol, cetomacrogol emulsifying wax, sorbitan esters, polyoxyethylene alkyl ethers, e.g., macrogol ethers such as cetomacrogol 1000, polyoxyethylene castor oil derivatives, polyoxyethylene sorbitan fatty acid esters, e.g., the commercially available Tweens, polyethylene glycols, polyoxyethylene stearates, colloidol silicon dioxide, phosphates, sodium dodecylsulfate, carboxymethylcellulose calcium, carboxymethylcellulose sodium, methylcellulose, hydroxyethylcellulose, hydroxypropyl methycellulose phthalate, noncrystalline cellulose, magnesium aluminum silicate, triethanolamine, polyvinyl alcohol, and polyvinylpyrrolidone (PVP). Most of these excipients are described in detail in the *Handbook of Pharmaceutical Excipients*, published jointly by the American Pharmaceutical Association and The Pharmaceutical Society of Great Britain (The Pharmaceutical Press, 1986). The surface stabilizers are commercially available and/or can be prepared by techniques known in the art.

Particularly preferred surface stabilizers, which can be used in conjunction with the surface stabilizer, include polyvinyl pyrrolidone, Pluronic F68® and F108®, which are block copolymers of ethylene oxide and propylene oxide, Tetronic 908®, which is a tetrafunctional block copolymer derived from sequential addition of ethylene oxide and propylene oxide to ethylenediamine, dextran, lecithin, Aerosol OT®, which is a dioctyl ester of sodium sulfosuccinic acid, available from American Cyanamid, dioctyl sodium sulfosuccinate, Duponol P®, which is a sodium lauryl sulfate, available from DuPont, Triton X-200®, which is an alkyl aryl polyether sulfonate, available from Rohm and Haas, Tween 80®, which is a polyoxyethylene sorbitan fatty acid ester, available from ICI Specialty Chemicals, and Carbowax 3350® and 934®, which are polyethylene glycols available from Union Carbide.

Examples of filling agents are lactose monohydrate, lactose anhydrous, and various starches; examples of binding agents are various celluloses and cross-linked polyvinylpyrrolidone, microcrystalline cellulose, such as Avicel® PH101 and Avicel® PH102, microcrystalline cellulose, and silicified microcrystalline cellulose (SMCC). Examples of solid support that may be as a base for the spray dried or spray coated nanoparticulate composition include cellulose spheres such as microcrystalline cellulose spheres, starch spheres, sugar spheres, sugar-starch spheres, lactose spheres or other pharmaceutical excipients that are well known in the art.

Suitable lubricants, including agents that act on the flowability of the powder to be compressed, are sodium lauryl sulfate, colloidal silicon dioxide, such as Aerosil® 200, talc, stearic acid, magnesium stearate, calcium stearate, and silica gel.

Examples of sweeteners are any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like. Examples of preservatives are potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quarternary compounds such as benzalkonium chloride.

Suitable diluents include pharmaceutically acceptable inert fillers, such as microcrystalline cellulose, lactose, dibasic calcium phosphate, saccharides, and/or mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof. Examples of effervescent agents are effervescent couples such as a organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

The nanoparticulate compositions can be made using, for example, milling or precipitation techniques. Exemplary methods of making nanoparticulate compositions are described in U.S. Pat. Nos. 5,145,684 and 5,862,999.

The nanoparticulate drug particles of the present invention can be prepared by first dispersing the compound 2-(R)-(1-(R)-(3,5-bis(trifluoromethyl)-phenyl)ethoxy)-3-(S)-(4-fluoro)phenyl-4-(3-(5-oxo-1H,4H-1,2,4-triazolo)methylmorpholine in a liquid dispersion medium followed by applying mechanical means in the presence of grinding media to reduce the particle size of the active ingredient to an effective average particle size of less than about 1000 nm, preferably, less than about 400 nm, and more preferably, less than about 250 nm. The drug particles can be reduced in size in the presence of the surface stabilizer or the drug particles can be contacted with the surface stabilizer following attrition.

Milling of the compound 2-(R)-(1-(R)-(3,5-bis(trifluoromethyl)phenyl)-ethoxy)-3-(S)-(4-fluoro)phenyl-4-(3-(5-oxo-1H,4H-1,2,4-triazolo)methylmorpholine to obtain a nanoparticulate dispersion comprises dispersing particles of the compound 2-(R)-(1-(R)-(3,5-bis(trifluoromethyl)phenyl) ethoxy)-3-(S)-(4-fluoro)-phenyl-4-(3-(5-oxo-1H,4H-1,2,4- triazolo)methylmorpholine in a liquid dispersion medium, followed by applying mechanical means in the presence of grinding media to reduce the particle size of the compound to the desired effective average particle size. The particles of the compound can be reduced in size in the presence of at least one surface stabilizer. Alternatively, the particles of the compound can be contacted with one or more surface stabilizers after attrition. Other compounds, such as a diluent, can be added to the 2-(R)-(1-(R)-(3,5-bis(trifluoromethyl)phenyl) ethoxy)-3-(S)-(4-fluoro)phenyl-4-(3-(5-oxo-1H,4H-1,2,4-triazolo)methylmorpholine/surface stabilizer composition during the size reduction process. Dispersions can be manufactured continuously or in a batch mode. The resultant nanoparticulate dispersion can be utilized in solid or liquid dosage formulations, such as controlled release dosage formulations, solid dose fast melt formulations, aerosol formulations, tablets, capsules, etc.

Another method of forming the desired nanoparticulate composition is by microprecipitation. This is a method of preparing stable dispersions of the compound 2-(R)-(1-(R)-(3,5-bis(trifluoromethyl)phenyl)ethoxy)-3-(S)-(4-fluoro) phenyl-4-(3-(5-oxo-1H,4H-1,2,4-triazolo)methylmorpholine in the presence of one or more surface stabilizers and one or more colloid stability enhancing surface active agents free of any trace toxic solvents or solubilized heavy metal impurities. Such a method comprises, for example: (1) dissolving the compound 2-(R)-(1-(R)-(3,5-bis(trifluoromethyl)-phenyl)ethoxy)-3-(S)-(4-fluoro)phenyl-4-(3-(5-oxo-1H,4H-1,2, 4-triazolo)methyl-morpholine in a suitable solvent; (2) adding the formulation from step (1) to a solution comprising at least one surface stabilizer to form a clear solution; and (3) precipitating the formulation from step (2) using an appropriate non-solvent. The method can be followed by removal of any formed salt, if present, by dialysis or diafiltration and concentration of the dispersion by conventional means. The resultant nanoparticulate dispersion can be utilized in solid or liquid dosage formulations.

A general procedure for preparing the drug nanoparticles of the invention is set forth below. The active ingredient is either obtained commercially or prepared by techniques known in the art in a conventional coarse form. It is preferred, but not essential, that the particle size of the selected drug be less than about 100 μm as determined by sieve analysis. If the coarse particle size of the drug is greater than about 100 μm, then it is preferred that the drug particles be reduced in size to less than about 100 μm using a conventional milling method, such as airjet or fragmentation milling, prior to reducing the particulate drug to submicron particle size.

The coarse drug particles can then be added to a liquid medium in which the drug is essentially insoluble to form a premix. The concentration of the drug in the liquid medium can vary from about 0.1 to about 60%, but is preferably from about 5 to about 30% (w/w). It is preferred, but not essential, that the surface stabilizer is present in the premix. The concentration of the surface stabilizer can vary from about 0.1 to about 90%, but it is preferably from about 1 to about 75%, and more preferably from about 20 to about 60%, by weight based upon the total combined weight of the active ingredient and surface stabilizer. The apparent viscosity of the premix suspension is preferably less than about 1000 centipoise.

The premix can be used directly by subjecting it to mechanical means to reduce the average particle size in the dispersion to less than about 1000 nm, preferably, less than about 400 nm, more preferably, less than about 250 nm, and most preferably, less than about 100 nm. It is preferred that the premix be used directly when a ball mill is used for attrition. Alternatively, the active ingredient, and optionally the surface stabilizer, can be dispersed in the liquid medium using suitable agitation, such as a roller mill or a Cowles-type mixer, until a homogeneous dispersion is observed. In a homogeneous dispersion, no large agglomerates are visible to the naked eye. It is preferred that the premix be subjected to such a premilling dispersion step when a recirculating media mill is used for attrition.

The mechanical means applied to reduce the particle size of the active ingredient can be a dispersion mill. Suitable dispersion mills include, but are not limited to, a ball mill, an attritor mill, a vibratory mill, and media mills such as a sand mill or a bead mill. A media mill is preferred due to the relatively shorter milling time required to provide the desired reduction in particle size. For media milling, the apparent viscosity of the premix is preferably from about 100 to about 1000 centipoise. For ball milling, the apparent viscosity of the premix is preferably from about 1 to about 100 centipoise. Such ranges tend to afford an optimal balance between efficient particle fragmentation and media erosion.

The attrition time can vary widely and depends primarily upon the particular mechanical means and processing conditions selected. For ball mills, processing times of up to five days or longer may be required. Using a high shear media mill, processing times of less than 1 day (residence times of from one minute up to several hours) have provided the desired results.

The drug particles must be reduced in size at a temperature which does not significantly degrade the active ingredient. Processing temperatures of less than about 30-40° C. are ordinarily preferred. If desired, the processing equipment can be cooled with conventional cooling equipment. Generally, the methods of the invention can be conveniently carried out under conditions of ambient temperature and at processing pressures which are safe and effective for the milling process. For example, ambient processing pressures are typical of ball mills, attritor mills, and vibratory mills. Control of the temperature, for example, by jacketing or immersion of the milling chamber in ice water, is encompassed by the invention.

Processing pressures from about 1 psi (0.07 kg/cm2) up to about 50 psi (3.5 kg/cm2) are encompassed by the invention. Processing pressures typically range from about 10 psi to about 20 psi.

The surface stabilizer, if not present in the premix, must be added to the dispersion after attrition in an amount as described for the premix above. Thereafter, the dispersion can be mixed by, for example, shaking vigorously. Optionally, the dispersion can be subjected to a sonication step using, for example, an ultrasonic power supply. In such a method, the ultrasonic power supply can, for example, release ultrasonic energy having a frequency of about 20 to about 80 kHz for a time of about 1 to about 120 seconds.

After attrition is completed, the grinding media is separated from the milled particulate product using conventional separation techniques, such as by filtration, sieving through a mesh screen, and the like. The surface stabilizer be added to the milled particulate product either before or after the milled product is separated from the grinding media.

In a preferred grinding process, the particles are made continuously. In such a continuous method, the slurry of active ingredient/surface stabilizer and optionally an additional surface stablizer is continuously introduced into a milling chamber, the active ingredient is continuously contacted with grinding media while in the chamber to reduce the particle size of the active ingredient, and the active ingredient is continuously removed from the milling chamber. The surface stabilizer, either alone or in conjunction with one or more additional surface stabilizers, can also be continuously added to the media chamber along with the active ingredient, or it can be added to the active ingredient which is removed from the chamber following grinding.

The resulting dispersion of the present invention is stable and comprises the liquid dispersion medium described above. The dispersion of surface stabilizer and nanoparticulate active ingredient can be spray dried, spray coated onto a solid support such as cellulose spheres or sugar spheres or other pharmaceutical excipients using techniques well known in the art.

The grinding media for the particle size reduction step can be selected from rigid media which is preferably spherical or particulate in form and which has an average size of less than about 3 mm and, more preferably, less than about 1 mm. Such media can provide the desired drug particles of the invention with shorter processing times and impart less wear to the milling equipment. The selection of material for the grinding media is not believed to be critical. Zirconium oxide, such as 95% ZrO stabilized with yttrium and 95% ZrO stabilized with magnesia, zirconium silicate, and glass grinding media have been found to provide particles having acceptable minimal levels of contamination for the preparation of pharmaceutical compositions. Other media, such as stainless steel, titania, and alumina can also be used. Preferred grinding media have a density greater than about 3 g/cm$^3$.

The grinding media can comprise particles, preferably spherical in shape, such as beads, consisting of essentially polymeric resin. Alternatively, the grinding media can comprise particles having a core with a coating of the polymeric resin adhered thereto. The media can range in size from about 0.1 to about 3 mm. For fine grinding, the particles preferably are from about 0.2 to about 2 mm, and more preferably, from about 0.25 to about 1 mm in size.

The polymeric resin can have a density from about 0.8 to about 3.0 g/cm$^3$. Higher density resins are preferred as such resins can provide more efficient particle size reduction.

In general, polymeric resins suitable for use in the present invention are chemically and physically inert, substantially free of metals, solvent, and monomers, and of sufficient hardness and friability to enable them to avoid being chipped or crushed during grinding. Suitable polymeric resins include, but are not limited to, cross-linked polystyrenes, such as polystyrene cross-linked with divinylbenzene, styrene copolymers, polycarbonates, polyacetals such as Delrin®, vinyl chloride polymers and copolymers, polyurethanes, polyamides, poly(tetrafluoroethylenes), such as Teflon® and other fluoropolymers, high density polyethylenes, polypropylenes, cellulose ethers and esters such as cellulose acetate, polyhydroxymethacrylate, polyhydroxyethyl acrylate, silicone containing polymers such as polysiloxanes, and the like. The polymer can also be biodegradable. Exemplary biodegradabe polymers include, but are not limited to, poly(lactides), poly(glycolide) copolymers of lactides and glycolide, polyanhydrides, poly(hydroxy-ethyl methacylate), poly (imino carbonates), poly(N-acylhydroxyproline)esters, poly (N-palmitoyl hydroxyproline)esters, ethylene-vinyl acetate copolymers, poly(orthoesters), poly(caprolactones), and poly(phoshazenes). For biodegradable polymers, contamination of the resultant composition from the media itself can advantageously metabolize in vivo into biologically acceptable products that can be eliminated from the body.

The grinding media is separated from the milled particulate active ingredient using conventional separation techniques in a secondary process, such as by filtration, sieving through a mesh filter or screen, and the like. Other separation techniques such as centrifugation may also be employed.

As used herein, particle size is determined on the basis of the average particle size as measured by conventional techniques well known to those skilled in the art, such as sedimentation field flow fractionation, photon correlation spectroscopy, or disk centrifugation. When photon correlation spectroscopy (PCS) is used as the method of particle sizing, the average particle diameter is the Z-average particle diameter known to those skilled in the art. By "an average effective particle size of less than about 1000 nm," it is meant that at least 90% of the particles, by weight, have a particle size of less than about 1000 nm when measured by the above-noted techniques. In a preferred embodiment of the invention, the effective average particle size is less than about 400 nm, more preferred is less than about 250 nm, and in an even more preferred embodiment, the effective average particle size is less than about 100 nm. It is preferred that at least 95% and, more preferably, at least 99% of the particles have a particle size less than the effective average, e.g., 1000 nm. In a particularly preferred embodiment, essentially all of the particles have a size of less than about 400 nm, in a more preferred embodiments, essentially all of the particles have a size of less than about 250 nm, and in a most preferred embodiment, essentially all of the particles have a size of less than about 100 nm.

An exemplary process for preparing nanoparticulate active ingredients in a tablet formulation comprises: (1) using the method described below to obtain spray-dried nanoparticles of the desired active ingredient; (2) sieve-screening the spray-dried nanoparticles to obtain uniform particles of less than about 20 mesh; (3) blending the nanoparticulate active ingredient with tableting excipients; (4) compressing the uniform particles into tablets using a tableting apparatus; and (5) film coating the tablets.

The spray drying process is used to obtain an "intermediate" nanoparticulate powder subsequent to the milling process used to transform the active ingredient into nanoparticles. In an exemplary spray drying process, the high-solids active ingredient nanosuspension and the surface stabilizer are fed to an atomizer using a peristatic pump and atomized into a fine spray of droplets. The spray is contacted with hot air in the drying chamber resulting in the evaporation of moisture from the droplets. The resulting spray is passed into a cyclone where the powder is separated and collected. Alternatives to spray drying include fluid bed granulation, spray dry granulation, rotogranulation, fluid bed/spray drying granulation, extrusion and spheronization.

At the completion of the spray drying process, the collected spray-dried intermediate comprises the nanoparticles of the active ingredient suspended in a solid polymer matrix of the surface stabilizer. The moisture content of the intermediate is controlled by the operating conditions of the spray drying process. The characteristics of the nanoparticulate powder are critical to the development of a free flowing powder that can be blended with other excipients suitable for a directly compressible tablet formulation.

Tablets can be made using a direct compression tablet process or using a roller compaction process. In an exemplary direct compression process, the spray-dried intermediate and stabilizer are sieved through a screen and the screened material is blended. The desired excipients are sieved and added to the blender. At the completion of blending, the contents of the blender can be discharged into a tared collection container and compression of tablet cores can be completed on a tablet press. The blended material can be fed into a feed hopper and force-fed into the die cavities using an automatic feeder. The tablet press operating conditions can be set to meet thickness, hardness, and weight specifications. Upon completion of the compression operation, a film-coating can be applied to the tablet cores using, for example, a Vector-Freund Hi-Coated machine.

In an exemplary roller compaction process following the media milling process, the nanoparticulate drug suspension can be spray dried to form an intermediate. The spray dryer can be assembled in a co-current configuration using a rotary atomization nozzle and the nanosuspension can be fed to the rotary atomizer using a peristaltic pump. Acceptable spray-dried product has a moisture content which does not exceed 1.0% (w/w).

A dry granulation operation can be used to manufacture tablets comprising the active ingredient. Required amounts of the active ingredient/surface stabilizer spray-dried intermediate and appropriate excipients can be screened and blended. The blended material is then compacted using, for example, a roller compactor. The compacted material can then be granulated. Following granulation, additional excipients can be screened and blended with the granulation. The blended materials can then be compressed into tablets using a tablet press followed by coating.

In general, the pharmaceutical composition of the present invention comprises the compound 2-(R)-(1-(R)-(3,5-bis(trifluoromethyl)-phenyl)ethoxy)-3-(S)-(4-fluoro)phenyl-4-(3-(5-oxo-1H,4H-1,2,4-triazolo)methyl-morpholine having a particle size of less than about 1000 nm and a surface stabilizer in a solid formulation. In a preferred embodiment, the pharmaceutical composition comprises the compound 2-(R)-(1-(R)-(3,5-bis(trifluoromethyl)-phenyl)ethoxy)-3-(S)-(4-fluoro)phenyl-4-(3-(5-oxo-1H,4H-1,2,4-triazolo)methyl-morpholine having a particle size of less than about 1000 nm, a surface stabilizer, a redispersing agent, a solid support, and a lubricant.

In an embodiment of the present invention the pharmaceutical composition comprises the compound 2-(R)-(1-(R)-(3,5-bis(trifluoromethyl)phenyl)-ethoxy)-3-(S)-(4-fluoro)phenyl-4-(3-(5-oxo-1H,4H-1,2,4-triazolo)methylmorpholine having a particle size of less than about 400 nm, a surface stabilizer, a redispersing agent, a solid support, and, optionally, a lubricant.

In a preferred embodiment of the present invention the pharmaceutical composition comprises the compound 2-(R)-(1-(R)-(3,5-bis(trifluoromethyl)phenyl)-ethoxy)-3-(S)-(4-fluoro)phenyl-4-(3-(5-oxo-1H,4H-1,2,4-triazolo)methyl-morpholine having a particle size of less than about 400 nm, a surface stabilizer which is hydroxypropyl cellulose, a redispersing agent which is sucrose, a solid support which is cellulose spheres, and, optionally, a lubricant which is sodium lauryl sulfate.

In specific embodiments of the present invention, the pharmaceutical composition may comprise the compound 2-(R)-(1-(R)-(3,5-bis(trifluoromethyl)-phenyl)ethoxy)-3-(S)-(4-fluoro)phenyl-4-(3-(5-oxo-1H,4H-1,2,4-triazolo)methyl-morpholine at a dosage strength that is selected from: 25 mg, 40 mg, 80 mg, 125 mg, 150 mg, 160 mg and 250 mg.

The concentration of the one or more surface stabilizers can vary from about 0.01 to about 90%, from about 1 to about 75%, from about 10 to about 60%, or from about 10 to about 30% by weight based on the total combined dry weight of the drug substance and surface stabilizer. The concentration of the compound 2-(R)-(1-(R)-(3,5-bis(trifluoromethyl)phenyl) ethoxy)-3-(S)-(4-fluoro)phenyl-4-(3-(5-oxo-1H,4H-1,2,4-triazolo)methylmorpholine can vary from about 99.99% to about 10%, from about 99% to about 25%, from about 90% to about 40%, or from about 90% to about 70% by weight based on the total combined dry weight of the compound, the surface stabilizer and other excipients.

The surface stabilizer is preferably present in an amount of about 0.1 to about 10 mg per square meter of surface area of the active ingredient, or in an amount of about 0.1 to about 90%, and more preferably about 5 to about 50% by weight based upon the total weight of the dry particle. Alternatively, the surface stabilizer is present at an amount of about 1-20% by weight, preferably about 2-15% by weight, and more preferably about 3-10% by weight.

The solid support is present at an amount of about 0-90% by weight, preferably about 5-80% by weight, and more preferably about 5-60% by weight. Preferred solid supports include, but are not limited to sugar, starch and cellulose, such microcrystalline cellulose, especially microcrystalline cellulose spheres.

The redispersing agent is present at an amount of about 0-50% by weight, preferably about 10-50% by weight, and more preferably about 10-40% by weight. Preferred redispersing agents include, but are not limited to sugars such as glucose, manitol, lactose, dextrose, xylitol or sucrose, especially sucrose.

The lubricant is present at an amount of about 0-5% by weight, preferably about 0-2% by weight, and more preferably about 0-1% by weight. Preferred lubricants include, but are not limited to sodium lauryl sulfate, colloidal silicon dioxide, talc, stearic acid, magnesium stearate, calcium stearate, and silica gel, especially sodium lauryl sulfate.

In a preferred embodiment, the pharmaceutical composition comprises about 0.1 to 90% by weight of the compound 2-(R)-(1-(R)-(3,5-bis(trifluoromethyl)-phenyl)ethoxy)-3-(S)-(4-fluoro)phenyl-4-(3-(5-oxo-1H,4H-1,2,4-triazolo)methyl-morpholine having a particle size of less than about 1000 nm, and about 0.1 to 50% by weight of a surface stabilizer.

In an embodiment of the present invention the pharmaceutical composition comprises the compound 2-(R)-(1-(R)-(3,5-bis(trifluoromethyl)phenyl)-ethoxy)-3-(S)-(4-fluoro)phenyl-4-(3-(5-oxo-1H,4H-1,2,4-triazolo)methylmorpholine having a particle size of less than about 400 nm, a surface stabilizer, a redispersing agent, a solid support, and a lubricant.

An embodiment of the invention is directed to pharmaceutical compositions which comprise about 5-60% by weight of 2-(R)-(1-(R)-(3,5-bis(trifluoromethyl)phenyl)ethoxy)-3-(S)-(4-fluoro)phenyl-4-(3-(5-oxo-1H,4H-1,2,4-triazolo)methyl-morpholine having a particle size of less than about 1000 nm; about 1-20% by weight of a surface stabilizer; about 0-50% by weight of a redispersing agent; about 0-90% by weight of a solid support; and about 0-5% by weight of a lubricant, wherein the sum of all the ingredients is 100%.

An embodiment of the invention is directed to pharmaceutical compositions which comprise about 25-50% by weight of 2-(R)-(1-(R)-(3,5-bis(tri-fluoromethyl)phenyl)ethoxy)-3-(S)-(4-fluoro)phenyl-4-(3-(5-oxo-1H,4H-1,2,4-triazolo)methylmorpholine having a particle size of less than about 1000 nm; about 5-15% by weight of a surface stabilizer; about 0-50% by weight of a redispersing agent; about 10-50% by weight of a solid support; and about 0-5% by weight of a lubricant, wherein the sum of all the ingredients is 100%.

An embodiment of the invention is directed to pharmaceutical compositions which comprise about 5-60% by weight of 2-(R)-(1-(R)-(3,5-bis(trifluoromethyl)phenyl)ethoxy)-3-(S)-(4-fluoro)phenyl-4-(3-(5-oxo-1H,4H-1,2,4-triazolo)methyl-morpholine having a particle size of less than about 1000 nm; about 1-20% by weight of hydroxypropyl cellulose; about 10-50% by weight of sucrose; about 5-80% by weight of microcrystalline cellulose; and about 0-5% by weight of sodium lauryl sulfate; wherein the sum of all the ingredients is 100%.

An embodiment of the invention is directed to pharmaceutical compositions which comprise about 10-50% by weight of 2-(R)-(1-(R)-(3,5-bis(trifluoromethyl)phenyl)ethoxy)-3-(S)-(4-fluoro)phenyl-4-(3-(5-oxo-1H,4H-1,2,4-triazolo)methylmorpholine having a particle size of less than about 1000 nm; about 2-15% by weight of hydroxypropyl cellulose; about 10-50% by weight of sucrose; about 5-60% by weight of microcrystalline cellulose; and about 0-2% by weight of sodium lauryl sulfate; wherein the sum of all the ingredients is 100%.

Another embodiment of the invention is directed to pharmaceutical compositions which comprises about 20% by weight of 2-(R)-(1-(R)-(3,5-bis(trifluoromethyl)phenyl)ethoxy)-3-(S)-(4-fluoro)phenyl-4-(3-(5-oxo-1H,4H-1,2,4-triazolo)methylmorpholine; about 4% by weight of hydroxypropyl cellulose; about 20% by weight of sucrose; about 55% by weight of microcrystalline cellulose; and about 0-1% by weight of sodium lauryl sulfate.

An embodiment of the invention is directed to pharmaceutical compositions which comprises about 30-45% by weight of 2-(R)-(1-(R)-(3,5-bis(trifluoromethyl)phenyl)ethoxy)-3-(S)-(4-fluoro)phenyl-4-(3-(5-oxo-1H,4H-1,2,4-triazolo)methyl-morpholine; about 5-10% by weight of hydroxypropyl cellulose; about 30-45% by weight of sucrose; about 15-20% by weight of microcrystalline cellulose; and about 0-0.5% by weight of sodium lauryl sulfate.

An embodiment of the invention is directed to pharmaceutical compositions which comprises about 37% by weight of 2-(R)-(1-(R)-(3,5-bis(trifluoromethyl)phenyl)ethoxy)-3-(S)-(4-fluoro)phenyl-4-(3-(5-oxo-1H,4H-1,2,4-triazolo)methyl-morpholine; about 7.5% by weight of hydroxypropyl cellulose; about 37% by weight of sucrose; about 18.2% by weight of microcrystalline cellulose; and about 0.3% by weight of sodium lauryl sulfate.

An embodiment of the invention is directed to pharmaceutical compositions which comprises about 37% by weight of 2-(R)-(1-(R)-(3,5-bis(trifluoromethyl)-phenyl)ethoxy)-3-(S)-(4-fluoro)phenyl-4-(3-(5-oxo-1H,4H-1,2,4-triazolo)methyl-morpholine; about 7.4% by weight of hydroxypropyl cellulose; about 37% by weight of sucrose; about 18% by weight of microcrystalline cellulose; about 0.1% by weight of sodium lauryl sulfate; and about 0.2% by weight of micronized sodium lauryl sulfate.

A specific embodiment of the invention is the pharmaceutical composition which comprises about 80 mg 2-(R)-(1-(R)-(3,5-bis(trifluoromethyl)-phenyl)ethoxy)-3-(S)-(4-fluoro)phenyl-4-(3-(5-oxo-1H,4H-1,2,4-triazolo)methylmorpholine; about 16 mg hydroxypropyl cellulose; about 80 mg sucrose; about 39 mg microcrystalline cellulose spheres; and about 0.5 mg sodium lauryl sulfate.

A specific embodiment of the invention is the pharmaceutical composition which comprises about 125 mg 2-(R)-(1-(R)-(3,5-bis(trifluoromethyl)-phenyl)ethoxy)-3-(S)-(4-fluoro)phenyl-4-(3-(5-oxo-1H,4H-1,2,4-triazolo)methylmorpholine; about 25 mg hydroxypropyl cellulose; about 125 mg sucrose; about 61 mg microcrystalline cellulose spheres; and about 1.1 mg sodium lauryl sulfate.

A specific embodiment of the invention is the pharmaceutical composition which comprises about 160 mg 2-(R)-(1-(R)-(3,5-bis(trifluoromethyl)-phenyl)ethoxy)-3-(S)-(4-fluoro)phenyl-4-(3-(5-oxo-1H,4H-1,2,4-triazolo)methylmorpholine; about 32 mg hydroxypropyl cellulose; about 160 mg sucrose; and about 78 mg microcrystalline cellulose spheres; and about 1 mg sodium lauryl sulfate.

The examples are provided for the purpose of further illustration only and it should be understood that the invention is not to be limited to the specific conditions or details described in these examples. Throughout the specification, any and all references to a publicly available document, including a U.S. patent, are specifically incorporated by reference. Exemplifying the invention is the preparation and use of the formulations disclosed herein.

The process for preparing nanoparticulate compositions of 2-(R)-(1-(R)-(3,5-bis(trifluoromethyl)phenyl)ethoxy)-3-(S)-(4-fluoro)phenyl-4-(3-(5-oxo-1H,4H-1,2,4-triazolo)methylmorpholine generally comprises slurry preparation, premilling, media milling, coating dispersion preparation, Wurster column coating, sieving, blending, and encapsulation.

A specific manufacturing process is as follows:
(a) making a slurry preparation by dispersing the compound 2-(R)-(1-(R)-(3,5-bis(trifluoromethyl)phenyl)ethoxy)-3-(S)-(4-fluoro)phenyl-4-(3-(5-oxo-1H,4H-1,2,4-triazolo)methylmorpholine and hydroxypropyl cellulose-SL in water,
(b) premilling the slurry with water and sodium lauryl sulfate,
(c) media millilng,
(d) addition of water and sucrose to prepare the coating dispersion,
(e) filtration,
(f) mixing,
(g) Wurster coating on microcrystalline cellulose spheres,
(h) sieving,
(i) blending with the addition of micronized sodium lauryl sulfate,
(j) subdivision of material, and
(k) encapsulation in capsules.

The processes described herein may be employed by those skilled in the art to prepare nanoparticulate compositions with different dosage strengths of 2-(R)-(1-(R)-(3,5-bis(trifluoromethyl)phenyl)ethoxy)-3-(S)-(4-fluoro)phenyl-4-(3-(5-oxo-1H,4H-1,2,4-triazolo)methylmorpholine (e.g. 25 mg, 40 mg, 50 mg, 80 mg, 100 mg, 125 mg, 150 mg, 160 mg, 250 mg, etc.)

Compositions of Specific Drug Capsule Formulations

| Component | Comp'n (% of fill weight) | Comp'n (mg) | Comp'n (mg) | Comp'n (mg) |
| --- | --- | --- | --- | --- |
| Bulk Drug | 37.05 | 80.0 | 125.0 | 160.0 |
| Hydroxypropyl Cellulose SL | 7.41 | 16.00 | 25.00 | 32.00 |
| Sodium Lauryl Sulfate NF | 0.14 | 0.30 | 0.48 | 0.60 |
| Sucrose NF | 37.05 | 80.0 | 125.0 | 160.0 |
| Microcrystalline Cellulose Spheres | 18.14 | 39.16 | 61.21 | 78.32 |
| Micronized Sodium Lauryl Sulfate | 0.21 | 0.45 | 0.67 | 0.90 |
| Capsule Fill Weight | — | 215.9 | 337.4 | 431.8 |

A slurry of 35 kg (29 wt. %) 2-(R)-(1-(R)-(3,5-bis(trifluoromethyl)phenyl)ethoxy)-3-(S)-(4-fluoro)phenyl-4-(3-(5-oxo-1H,4H-1,2,4-triazolo)methylmorpholine drug particles is prepared in an aqueous solution of hydroxypropyl cellulose-SL in a 150-L jacketed tank equipped with a 45° pitched blade turbine. The slurry is heated to approximately 70° C. and premilled at that temperature through an in-line Ikaworks mill to achieve particles having mean size less than 60 µm and D90 less than 150 µm. The premilled slurry is cooled to approximately 5° C. An aqueous solution of sodium lauryl sulfate (SLS) is added to the premilled slurry. The suspended solids are then micronized using a 10-L media mill filled with polystyrene media to produce a colloidal dispersion consisting of approximately 138 nm mean particles. The resulting colloidal dispersion is then discharged and stored at 5° C.

An aqueous solution of sucrose is prepared using a 45° pitched blade turbine impeller in a 60-L tank. An amount of sucrose solution, which provides 1 to 1 theoretical weight ratio of sucrose to 2-(R)-(1-(R)-(3,5-bis(trifluoromethyl)phenyl)-ethoxy)-3-(S)-(4-fluoro)phenyl-4-(3-(5-oxo-1H,4H-1,2,4-triazolo)methylmorpholine, is mixed with the colloidal dispersion using a 45° pitched blade turbine Lightnin mixer in the two stainless steel drums to obtain a 20 wt. % drug colloidal coating dispersion. The coating dispersions prepared using two milled batches (steps 1 to 5) are then filtered through an in-line 30 μm polypropylene filter. The filtering step is conducted to remove any potential attrited media generated during the media milling step. The coating dispersions from the two milled batches are then mixed in a 347-L tank using a 3-blade marine propeller Lightnin mixer to obtain a uniform colloidal coating dispersion.

The coating dispersion is sprayed onto microcrystalline cellulose (celphere) substrate-spheres to a target weight gain of 450 wt. % using a 24" Glatt Wurster coating column. The drug-coated beads are screened through a nominal 864 μm and 1532 μm sieve screen using a 30" Sweco sieve to remove the fines (<864 μm) and aggregates (>1532 μm) generated, respectively, which may have been generated during the coating process. The drug-coated beads between approximately 864 μm and approximately 1532 μm are blended with jet-milled sodium lauryl sulfate using a 300-L Bohle blender. The blended coated beads from the blender are discharged into batches or subbatches as desired.

A subbatch of the blended beads is filled into hard gelatin capsules to the target fill weight to provide 125-mg dose capsules. The target fill weight is based on the measured assay. Encapsulation is performed using a Bosch GKF 1500 capsule filler equipped with a pellet feeder and a 10 mm dosing chamber set for the #1 capsule size. Dosage forms of 25 mg, 40 mg, 50 mg, 80 mg, 100 mg, 150 mg, 160 mg and 250 mg are prepared in an identical manner, but using a different size and fill weight of capsule.

Slurry Preparation & Premilling: Place 77.61 kg USP Water at room temperature in a 150-L tank. With a 45° pitch-blade turbine rotating at approximately 175 rpm, add 7.000 kg of Hydroxypropyl Cellulose-SL (HPC-SL) slowly into the tank. Ensure that the liquid surface maintains a vortex during the HPC-SL addition by increasing the agitator speed if needed. Continue agitation for 90 minutes after HPC-SL addition to ensure that the HPC-SL is dissolved in water. With the 45° pitch-blade turbine rotating at approximately 200 rpm, add 35.00 kg 2-(R)-(1-(R)-(3,5-bis(trifluoromethyl) phenyl)ethoxy)-3-(S)-(4-fluoro)phenyl-4-(3-(5-oxo-1H,4H-1,2,4-triazolo)methylmorpholine slowly into the tank. Ensure that the liquid surface maintains a vortex during the compound addition by increasing the agitator speed if needed. Mix the slurry for 30 minutes at approximately 200 rpm. Initiate premilling of the slurry by flowing the slurry through the Ikaworks premill. Measure the drug particle size during premilling. Initiate cooling of the slurry to 5° C. The mixing speeds is maintained to ensure that the liquid surface is not vortexing, yet provide adequate mixing in the tank (i.e., fluids movement at the tank wall).

After the slurry has reached less than 30° C., stop the premilling. Prepare the sodium lauryl sulfate (SLS) solution by placing 948.5 g USP Water at room temperature in a stainless steel container with Lightnin stirrer rotating at approximately 400 rpm. Add 135.5 g SLS slowly into the stirred USP water and mix for 15 minutes. Add the SLS solution slowly to the 5° C. slurry in the tank with tank agitator rotating at approximately 200 rpm and mix for 15 minutes.

Media Milling: Ensure that the mill filter housing is equipped with 150 μm screen. Add 5.60 kg (approximately 87.5% media load) polymeric media into the mill. Initiate media milling of the slurry by circulating the slurry through the mill and starting the LMZ-10 mill agitator rotation. Conduct the milling with the slurry flow rates, slurry flow rate ramp rates, mill agitator speeds, and mill agitator speed ramp rates values essentially as listed below. Maintain the slurry/dispersion in the tank at 5° C. and the agitator speed at 200 rpm during the entire media milling run. Media milling parameters:

| Step | Parameters | Setting |
| --- | --- | --- |
| Prefill | Prefill flow rate, lpm | 0-3 |
| | Prefill volume, liters | 0-3 |
| Start up | Start-up flow rate, lpm | 0-3 |
| | Start-up flow rate ramp rate, lpm/min | 0-2 |
| | Steady-state flow rate ramp rate, lpm/min | 0-2 |
| | Initial milling volume, liters | 0-1200 |
| | Start-up agitator speed, rpm | 500-1300 |
| | Intermediate agitator speed, rpm | 500-1300 |
| | Agitator ramp rate 1, rpm/min | 0-1300 |
| Steady state | Steady-state flow rate, lpm | 0-20 |
| | Agitator final speed, rpm | 500-1300 |
| | Agitator ramp rate 2, rpm/min | 0-1300 |

Measure the drug particle size during media milling. The target particle size distribution is the average of the mean of three different samples is less than 138 nm the mean of each of the three samples is less than 144 nm the average of the D90 of the three samples is less than 216 nm the D90 of each of the three samples is less than 228 nm. Stop media milling (by shutting off the mill agitator rotation and dispersion circulation) only after confirming reduction to the above target particle size distribution. Discharge the colloidal dispersion into two stainless steel drums, seal the drums, and store them at 5° C.

Sucrose Solution & Colloidal Coating Dispersion: For each batch of the colloidal dispersion, the amount of sucrose and USP water required for preparing the sucrose solution will depend on the assay and the amount of colloidal dispersion recovered after the milling process. The targeted drug concentration of the coating dispersion is 20 wt. % with the theoretical weight ratio of sucrose to 2-(R)-(1-(R)-(3,5-bis (trifluoro-methyl)phenyl)ethoxy)-3-(S)-(4-fluoro)phenyl-4-(3-(5-oxo-1H,4H-1,2,4-triazolo)methylmorpholine being 1 to 1. Determine the amount of sucrose and USP water required for preparing the sucrose solution (for each batch) based on: Drug (kg) in the batch=(colloidal dispersion collected in kg)*(drug assay in mg drug/mg dispersion); Sucrose (kg) required for each batch=drug amount from above; Theoretical coating dispersion (kg) prepared=(5)*drug amount from above; Water (kg) for preparing sucrose solution=theoretical coating dispersion−colloidal dispersion collected−sucrose required; Theoretical sucrose solution (kg)= sucrose+water. Since each batch of the colloidal dispersion may be split into drums, the sucrose solution required for each drum is based on the actual colloidal dispersion present in each of the drums (as described above). In addition, excess sucrose solution is prepared for each batch.

Place the determined amount of USP Water in a 60-L tank. With the 45° pitch-blade turbine rotating at approximately 75 rpm, add the determined amount of sucrose slowly into the 60-L tank. Continue agitation for 90 minutes after sucrose addition to ensure that the sucrose is dissolved in water. Remove the drum of colloidal dispersion from cold storage. Start stirring the colloidal dispersion using the Lightnin mixer. Drain out amount of sucrose solution required for colloidal dispersion into a stainless steel container. Pour this sucrose solution slowly into the drum with continuous agitation and mix for 60 minutes. Transfer the coating dispersion from drum into another stainless drum through an in-line approximately 5 ft$^2$ 30 μm polypropylene capsule filter. Seal the drum containing the filtered coating dispersion and store it at 5° C. until transferred for coating.

Wurster Column Coating: Vacuum load 23.6 kg Microcrystalline cellulose spheres or celphere into a 24" coating column equipped with B & #0 base plates, 1.5 mm Schlick nozzle, 100 mesh screen on the base plates, 69 mesh exhaust filter, high-speed insert, insert extension, 40 mm partition gap, and two NIR probes in the annulus. Initiate heating of the celphere at an inlet process air flow rate of 900 scfm, temperature at 80° C., and dew point at 12° C. Maintain the atomizing air flow at 5 scfm during the heating period. Initiate coating with atomizing air flow rate at 25 scfm when the bed temperature exceeds 70° C. Maintain the inlet air flow rate between 500 and 2500 scfm and spray rate profiles between 200 and 900 g/min during coating. Stop spraying when an appropriate coating dispersion has been sprayed. Reduce the atomizer air to 5 scfm and dry the coated beads for 5 minutes using inlet process air at 80° C., 900 scfm, and 12° C. dew point. After 5 minutes of drying, initiate cooling by reducing the inlet process air flow rate temperature to 25° C. Stop the air flow when the bed temperature reaches less than 45° C. Discharge the coated beads into fiber drum lined with double polyethylene bags.

Sieving: Set a 30" Sweco sieve shaker with 864 μm screen below the 1532 μm screen. With the sieve shaker vibrating, manually pour all the coated beads slowly above the 1532 μm screen. Collect the coated beads less than 864 μm, between 864 μm and 1532 μm, and above 1532 μm separately into fiber drums lined with double polyethylene bags. Seal the drum and store until further processing.

Blending: Load the coated beads (between 864 μm and 1532 μm) into a 300-L Bohle blender. Screen 260 g micronized/jet-milled sodium lauryl sulfate (SLS) through a 60 mesh screen on top of the coated beads in the blender. (The SLS is micronized to minimize its segregation from the coated beads.) Blend the coated beads with the micronized sodium lauryl sulfate by rotating the blender at 6 rpm for 15 minutes. Discharge the blended beads into six sub batches of 41.5 kg, 27.0 kg, 22.0 kg, 13.5 kg, 13.0 kg, and remainder (approximately 13.0 kg) into six fiber drums lined with double polyethylene bags. Store the blended beads until further processing.

Encapsulation: Set a Bosch GKF 1500 encapsulator with a pellet feeder and a 10 mm dosing chamber for the particular capsule size. Set the encapsulator speed at 75 stations per minute. Load the capsules into the capsule hopper. Load the blended beads into the pellet feeder hopper. Determine the target fill weight based on the assay of the blended coated beads and the target capsule fill weight. Start the encapsulation after adjusting the chamber volume to achieve the target filled capsule weights at 75 stations per minute encapsulator speed. Maintain the target filled capsule weight within the above upper and lower limits. If necessary, adjust the chamber volume to maintain the desired target weight. Discharge the filled capsules into fiber drums lined with double polyethylene bags. Store the capsule product until they are transferred for packaging.

The pharmaceutical compositions of the present invention can be administered to humans and animals in any pharmaceutically acceptable manner, such as orally, via pulmonary route, rectally, parenterally (intravenous, intramuscular, or subcutaneous), intracisternally, intravaginally, intraperitoneally, locally (powders, ointments or drops), or as a buccal or nasal spray.

For preparing solid compositions such as tablets, the nanoparticulate composition is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

For the treatment of the clinical conditions and diseases noted above, the formulations of this invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

The pharmaceutical compositions of the present invention are useful in the prevention and treatment of a wide variety of clinical conditions in a subject which are characterized by the presence of an excess of tachykinin, in particular substance P, activity. Thus, for example, an excess of tachykinin, and in particular substance P, activity is implicated in a variety of disorders of the central nervous system. Such disorders include mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders; schizophrenia and other psychotic disorders, for example, schizophreniform disorders, schizoaffective disorders, delusional disorders, brief psychotic disorders, shared psychotic disorders and psychotic disorders with delusions or hallucinations; delerium, dementia, and amnestic and other cognitive or neurodegenerative disorders, such as Alzheimer's disease, senile dementia, dementia of the Alzheimer's type, vascular dementia, and other dementias, for example, due to HIV disease, head trauma, Parkinson's disease, Huntington's disease, Pick's disease, Creutzfeldt-Jakob disease, or due to multiple aetiologies; Parkinson's disease and other extra-pyramidal movement disorders such as medication-induced movement disorders, for example, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremour; substance-related disorders arising from the use of alcohol, amphetamines (or amphetamine-like substances) caffeine, cannabis, cocaine, hallucinogens, inhalants and aerosol propellants, nicotine, opioids, phenylglycidine derivatives, sedatives, hypnotics, and anxiolytics, which substance-related disorders include dependence and abuse, intoxication, withdrawal, intoxication delerium, withdrawal delerium, persisting dementia, psychotic disorders, mood disorders, anxiety disorders, sexual dysfunction and sleep disorders; epilepsy; Down's syndrome; demyelinating diseases such as MS and ALS and other neuropathological disorders such as peripheral neuropathy, for example diabetic and chemotherapy-induced neuropathy, and postherpetic neuralgia, trigeminal neuralgia, segmental or intercostal neuralgia and other neuralgias; and cerebral vascular disorders due to acute or chronic cerebrovascular damage such as cerebral infarction, subarachnoid haemorrhage or cerebral oedema.

Tachykinin, and in particular substance P, activity is also involved in nociception and pain. The formulations of the present invention will therefore be of use in the prevention or treatment of diseases and conditions in which pain predominates, including soft tissue and peripheral damage, such as acute trauma, osteoarthritis, rheumatoid arthritis, musculoskeletal pain, particularly after trauma, spinal pain, myofascial pain syndromes, headache, episiotomy pain, and burns; deep and visceral pain, such as heart pain, muscle pain, eye pain, orofacial pain, for example, odontalgia, abdominal pain, gynaecological pain, for example, dysmenorrhoea, and labour pain; pain associated with nerve and root damage, such as pain associated with peripheral nerve disorders, for example, nerve entrapment and brachial plexus avulsions, amputation, peripheral neuropathies, tic douloureux, atypical facial pain, nerve root damage, and arachnoiditis; pain associated with carcinoma, often referred to as cancer pain; central nervous system pain, such as pain due to spinal cord or brain stem damage; low back pain; sciatica; ankylosing spondylitis, gout; and scar pain.

Tachykinin, and in particular substance P, antagonists may also be of use in the treatment of respiratory diseases, particularly those associated with excess mucus secretion, such as chronic obstructive airways disease, bronchopneumonia, chronic bronchitis, cystic fibrosis and asthma, adult respiratory distress syndrome, and bronchospasm; inflammatory diseases such as inflammatory bowel disease, psoriasis, fibrositis, osteoarthritis, rheumatoid arthritis, pruritis and sunburn; allergies such as eczema and rhinitis; hypersensitivity disorders such as poison ivy; ophthalmic diseases such as conjunctivitis, vernal conjunctivitis, and the like; ophthalmic conditions associated with cell proliferation such as proliferative vitreoretinopathy; cutaneous diseases such as contact dermatitis, atopic dermatitis, urticaria, and other eczematoid dermatitis.

Tachykinin, and in particular substance P, antagonists may also be of use in the treatment of neoplasms, including breast tumours, neuroganglioblastomas and small cell carcinomas such as small cell lung cancer.

Tachykinin, and in particular substance P, antagonists may also be of use in the treatment of gastrointestinal (GI) disorders, including inflammatory disorders and diseases of the GI tract such as gastritis, gastroduodenal ulcers, gastric carcinomas, gastric lymphomas, disorders associated with the neuronal control of viscera, ulcerative colitis, Crohn's disease, irritable bowel syndrome and emesis, including acute, delayed or anticipatory emesis such as emesis induced by chemotherapy, radiation, toxins, viral or bacterial infections, pregnancy, vestibular disorders, for example, motion sickness, vertigo, dizziness and Meniere's disease, surgery, migraine, variations in intercranial pressure, gastro-oesophageal reflux disease, acid indigestion, over indulgence in food or drink, acid stomach, waterbrash or regurgitation, heartburn, for example, episodic, nocturnal or meal-induced heartburn, and dyspepsia.

Tachykinin, and in particular substance P, antagonists may also be of use in the treatment of a variety of other conditions including stress related somatic disorders; reflex sympathetic dystrophy such as shoulder/hand syndrome; adverse immunological reactions such as rejection of transplanted tissues and disorders related to immune enhancement or suppression such as systemic lupus erythematosus; plasma extravasation resulting from cytokine chemotherapy, disorders of bladder function such as cystitis, bladder detrusor hyper-reflexia and incontinence; fibrosing and collagen diseases such as scleroderma and eosinophilic fascioliasis; disorders of blood flow caused by vasodilation and vasospastic diseases such as angina, vascular headache, migraine and Reynaud's disease; and pain or nociception attributable to or associated with any of the foregoing conditions, especially the transmission of pain in migraine.

The pharmaceutical compositions of the present invention are also of value in the treatment of a combination of the above conditions, in particular in the treatment of combined post-operative pain and post-operative nausea and vomiting.

The pharmaceutical compositions of the present invention are particularly useful in the treatment of emesis, including acute, delayed or anticipatory emesis, such as emesis induced by chemotherapy, radiation, toxins, pregnancy, vestibular disorders, motion, surgery, migraine, and variations in intercranial pressure. Most especially, the pharmaceutical compositions of the present invention are of use in the treatment of emesis induced by antineoplastic (cytotoxic) agents, including those routinely used in cancer chemotherapy, and emesis induced by other pharmacological agents, for example, rolipram.

Examples of such chemotherapeutic agents include alkylating agents, for example, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of podophyllotoxin; and cytotoxic antibiotics. Commonly used chemotherapeutic agents include cisplatin, dacarbazine (DTIC), dactinomycin, mechlorethamine, streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin and chlorambucil.

The pharmaceutical compositions of the present invention are also of use in the treatment of emesis induced by radiation including radiation therapy such as in the treatment of cancer; and in the treatment of post-operative nausea and vomiting.

It will be appreciated that the compounds of the present invention may be presented together with another therapeutic agent as a combined preparation for simultaneous, separate or sequential use for the relief of emesis or post-operative nausea and vomiting.

A further aspect of the present invention comprises the compounds of the present invention in combination with a 5-$HT_3$ antagonist, such as ondansetron, granisetron or tropisetron, or other anti-emetic medicaments, for example, a dopamine antagonist such as metoclopramide or domperidone or $GABA_B$ receptor agonists such as baclofen. Additionally, a pharmaceutical composition of the present invention, either alone or in combination with one or more other anti-emetic therapeutic agents, may be administered in combination with an anti-inflammatory corticosteroid, such as dexamethasone, betamethasone, triamcinolone, triamcinolone acetonide, flunisolide, budesonide, or other Dexamethasone (Decadron™) is particularly preferred. Furthermore, a pharmaceutical composition of the present invention may be administered in combination with a chemotherapeutic agent such as an alkylating agent, antimetabolite, mitotic inhibitor or cytotoxic antibiotic, as described above. In general, the currently available dosage forms of the known therapeutic agents for use in such combinations will be suitable.

The pharmaceutical compositions of the present invention are also particularly useful in the treatment of pain or nociception and/or inflammation and disorders associated therewith such as, for example, neuropathy, such as diabetic and chemotherapy-induced neuropathy, postherpetic and other neuralgias, asthma, osteroarthritis, rheumatoid arthritis and headache, including migraine, acute or chronic tension headache, cluster headache, temporomandibular pain, and maxillary sinus pain.

The pharmaceutical compositions of the present invention are also particularly useful in the treatment of depression including depressive disorders, for example, single episodic or recurrent major depressive disorders, and dysthymic disorders, depressive neurosis, and neurotic depression; melancholic depression including anorexia, weight loss, insomnia and early morning waking, and psychomotor retardation; atypical depression (or reactive depression) including increased appetite, hypersomnia, psychomotor agitation or irritability, anxiety and phobias; seasonal affective disorder; or bipolar disorders or manic depression, for example, bipolar I disorder, bipolar II disorder and cyclothymic disorder.

A further aspect of the present invention comprises the use of a pharmaceutical composition of the present invention for achieving a chronobiologic (circadian rhythm phase-shifting) effect and alleviating circadian rhythm disorders in a patient. The present invention is further directed to the use of a pharmaceutical composition of the present invention for blocking the phase-shifting effects of light in a patient.

The present invention further relates to the use of a pharmaceutical composition of the present invention for enhancing or improving sleep quality, in particular by increasing sleep efficiency and augmenting sleep maintenance, as well as for preventing and treating sleep disorders and sleep disturbances, in a patient.

In a preferred embodiment, the present invention provides a method for the phase advance or phase delay in the circadian rhythm of a subject which comprises administering to the subject an appropriate amount of a pharmaceutical composition of the present invention or a pharmaceutically acceptable salt thereof.

The present invention is further directed to the use of a pharmaceutical composition of the present invention or a pharmaceutically acceptable salt thereof, for enhancing or improving sleep quality as well as preventing and treating sleep disorders and sleep disturbances in a patient. In particular, the present invention provides a method for enhancing or improving sleep quality by increasing sleep efficiency and augmenting sleep maintenance. In addition, the present invention provides a method for preventing and treating sleep disorders and sleep disturbances in a patient which comprising the administration of a pharmaceutical composition of the present invention or a pharmaceutically acceptable salt thereof. The present invention is useful for the treatment of sleep disorders, including Disorders of Initiating and Maintaining Sleep (insomnias) ("DIMS") which can arise from psychophysiological causes, as a consequence of psychiatric disorders (particularly related to anxiety), from drugs and alcohol use and abuse (particularly during withdrawal stages), childhood onset DIMS, nocturnal myoclonus and restless legs and non specific REM disturbances as seen in ageing, including insomnia and fibromyalgia.

The pharmaceutical compositions of this invention may be administered to patients (animals and humans) in need of such treatment in dosages that will provide optimal pharmaceutical efficacy. It will be appreciated that the dose required for use in any particular application will vary from patient to patient, not only with the particular pharmaceutical composition or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day.

For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The pharmaceutical compositions may be administered on a regimen of 1 to 4 times per day, preferably once or twice per day.

In the treatment of emesis, a suitable dosage level is about 0.001 to 10 mg/kg per day, preferably about 0.005 to 5 mg/kg per day, and especially 0.01 to 3 mg/kg per day. For example, the pharmaceutical compositions may be administered on a regimen of 1 to 4 times per day, preferably once or twice per day at a dosage strength of 25 mg, 40 mg, 80 mg, 100 mg, 125 mg, 150 mg, 160 mg, 250 mg, etc.

In the treatment of psychiatric disorders, a suitable dosage level is about 0.001 to 10 mg/kg per day, preferably about 0.005 to 5 mg/kg per day, and especially 0.01 to 3 mg/kg per day. The pharmaceutical compositions may be administered on a regimen of 1 to 4 times per day, preferably once or twice per day. For example, the pharmaceutical compositions may be administered on a regimen of 1 to 4 times per day, preferably once or twice per day at a dosage strength of 25 mg, 40 mg, 80 mg, 100 mg, 125 mg, 150 mg, 160 mg, 250 mg, etc.

The present invention further provides a pharmaceutical composition of the present invention for use in therapy. According to a further or alternative aspect, the present invention provides a pharmaceutical composition of the present invention for use in the manufacture of a medicament for the treatment of physiological disorders associated with an excess of tachykinins, especially substance P. The present invention also provides a method for the treatment or prevention of physiological disorders associated with an excess of tachykinins, especially substance P, which method comprises administration to a patient in need thereof of a tachykinin reducing amount of a pharmaceutical composition of the present invention.

According to a further aspect of the present invention, it may be desirable to treat any of the aforementioned conditions with a combination of a pharmaceutical composition according to the present invention and one or more other pharmacologically active agents suitable for the treatment of the specific condition. The pharmaceutical composition of the present invention and the other pharmacologically active agent(s) may be administered to a patient simultaneously, sequentially or in combination. For example, the present pharmaceutical composition may employed directly in combination with the other active agent(s), or it may be administered prior, concurrent or subsequent to the administration of the other active agent(s). In general, the currently available dosage forms of the known therapeutic agents for use in such combinations will be suitable.

For example, a pharmaceutical composition of the present invention may be presented together with another therapeutic agent as a combined preparation for simultaneous, separate, or sequential use for the relief of emesis. Such combined preparations may be, for example, in the form of a twin pack. A preferred combination comprises a pharmaceutical composition of the present invention with a chemotherapeutic agent such as an alkylating agent, antimetabolite, mitotic inhibitor, or cytotoxic antibiotic, as described above.

For the prevention or treatment of emesis a pharmaceutical composition of the present invention may additionally comprise other anti-emetic agents, especially $5HT_3$ receptor antagonists, such as ondansetron, granisetron, tropisetron, decadron, and zatisetron, or $GABA_B$ receptor agonists, such as baclofen. Likewise, for the prevention or treatment of migraine a pharmaceutical composition of the present invention may additionally comprise other anti-migraine agents, such as ergotamines or $5HT_1$ agonists, especially sumatriptan.

It will be appreciated that for the treatment or prevention of migraine, a pharmaceutical composition of the present invention may additionally comprise other anti-migraine agents, such as ergotamines or $5\text{-}HT_1$ agonists, especially sumatriptan, naratriptan, zolmatriptan or rizatriptan.

It will be appreciated that for the treatment or prevention of pain or nociception or inflammatory diseases, a pharmaceutical composition of the present invention may additionally comprise an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a pharmaceutical composition such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the instant pharmaceutical compositions may additionally comprise a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine.

In a further or alternative aspect of the present invention, there is provided a product comprising a pharmaceutical composition of the present invention and an analgesic as a combined preparation for simultaneous, separate or sequential use in the treatment or prevention of pain or nociception.

It will be appreciated that for the treatment of depression or anxiety, a pharmaceutical composition of the present invention may additionally comprise other anti-depressant or anti-anxiety agents.

Suitable classes of anti-depressant agent include norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists and atypical anti-depressants. Suitable norepinephrine reuptake inhibitors include tertiary amine tricyclics and secondary amine tricyclics. Suitable examples of tertiary amine tricyclics include: amitriptyline, clomipramine, doxepin, imipramine and trimipramine, and pharmaceutically acceptable salts thereof. Suitable examples of secondary amine tricyclics include: amoxapine, desipramine, maprotiline, nortriptyline and protriptyline, and pharmaceutically acceptable salts thereof. Suitable selective serotonin reuptake inhibitors include: fluoxetine, fluvoxamine, paroxetine and sertraline, and pharmaceutically acceptable salts thereof. Suitable monoamine oxidase inhibitors include: isocarboxazid, phenelzine, tranylcypromine and selegiline, and pharmaceutically acceptable salts thereof. Suitable reversible inhibitors of monoamine oxidase include: moclobemide, and pharmaceutically acceptable salts thereof. Suitable serotonin and noradrenaline reuptake inhibitors of use in the present invention include: venlafaxine, and pharmaceutically acceptable salts thereof. Suitable atypical anti-depressants include: bupropion, lithium, nefazodone, trazodone and viloxazine, and pharmaceutically acceptable salts thereof. Suitable classes of anti-anxiety agent include benzodiazepines and $5\text{-}HT_{1A}$ agonists or antagonists, especially $5\text{-}HT_{1A}$ partial agonists, and corticotropin releasing factor (CRF) antagonists. Suitable benzodiazepines include: alprazolam, chlordiazepoxide, clonazepam, chlorazepate, diazepam, halazepam, lorazepam, oxazepam and prazepam, and pharmaceutically acceptable salts thereof. Suitable $5\text{-}HT_{1A}$ receptor agonists or antagonists include, in particular, the $5\text{-}HT_{1A}$ receptor partial agonists buspirone, flesinoxan, gepirone and ipsapirone, and pharmaceutically acceptable salts thereof.

Therefore, in a further aspect of the present invention, there is provided a pharmaceutical composition comprising a nanoparticulate composition of the present invention and an anti-depressant or anti-anxiety agent, together with at least one pharmaceutically acceptable carrier or excipient.

In a further or alternative aspect of the present invention, there is provided a product comprising a nanoparticulate composition of the present invention and an anti-depressant or anti-anxiety agent as a combined preparation for simultaneous, separate or sequential use for the treatment or prevention of depression and/or anxiety.

It will be appreciated that for the treatment or prevention of eating disorders, including obesity, bulimia nervosa and compulsive eating disorders, a pharmaceutical composition of the present invention may additionally comprise other anorectic agents.

It will be appreciated that when using any combination described herein, both the pharmaceutical composition of the present invention and the other active agent(s) will be administered to a patient, within a reasonable period of time. The pharmaceutical compositions may be in the same pharmaceutically acceptable carrier and therefore administered simultaneously. They may be in separate pharmaceutical carriers such as conventional oral dosage forms which are taken simultaneously. The term "combination" also refers to the case where the pharmaceutical compositions are provided in separate dosage forms and are administered sequentially. Therefore, by way of example, one active component may be administered as a tablet and then, within a reasonable period of time, the second active component may be administered either as an oral dosage form such as a tablet or a fast-dissolving oral dosage form. By "reasonable period of time" is meant a time period that is not in excess of about 1 hour. That is, for example, if the first active component is provided as a tablet, then within one hour, the second active component should be administered, either in the same type of dosage form, or another dosage form which provides effective delivery of the medicament.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A nanoparticulate composition comprising the compound 2-(R)-(1-(R)-(3,5-bis(trifluoromethyl)phenyl)ethoxy)-3-(S)-(4-fluoro)phenyl-4-(3-(5-oxo-1H,4H-1,2,4-triazolo)methylmorpholine, or a pharmaceutically acceptable salt thereof, the compound having adsorbed on the surface thereof at least one surface stabilizer in an amount sufficient to maintain an effective average particle size of less than 400 nm, wherein the surface stabilizer is selected from the group consisting of hydroxypropyl cellulose-super low viscosity and sodium lauryl sulfate.

2. The composition of claim 1 wherein the nanoparticles have an effective average particle size of less than 250 nm.

3. A pharmaceutical composition comprising the nanoparticulate composition of claim 1 and a pharmaceutically acceptable carrier.

4. A pharmaceutical composition comprising the nanoparticulate composition of claim 1 which has been spray dried or spray coated on a solid support.

5. The pharmaceutical composition of claim 4 wherein the solid support is selected from microcrystalline cellulose spheres, sugar-starch spheres and lactose spheres.

6. A pharmaceutical composition comprising the compound 2-(R)-(1-(R)-(3,5-bis(trifluoromethyl)phenyl)ethoxy)-3-(S)-(4-fluoro)phenyl-4-(3-(5-oxo-1H,4H-1,2,4-triazolo)methylmorpholine having a particle size of less than 400 nm, a surface stabilizer, a redispersing agent and a solid support, wherein the surface stabilizer is selected from the group consisting of hydroxypropyl cellulose-super low viscosity and sodium lauryl sulfate.

7. The pharmaceutical composition of claim 6 comprising about 5-60% by weight of 2-(R)-(1-(R)-(3,5-bis(trifluoromethyl)phenyl)ethoxy)-3-(S)-(4-fluoro)-phenyl-4-(3-(5-oxo-1H,4H-1,2,4-triazolo)methylmorpholine having a particle size of less than 400 nm; about 1-20% by weight of a surface stabilizer; about 0-50% by weight of a redispersing agent; about 0-90% by weight of a solid support; and about 0-5% by weight of a lubricant.

8. The pharmaceutical composition of claim 7 comprising about 25-50% by weight of 2-(R)-(1-(R)-(3,5-bis(trifluoromethyl)phenyl)ethoxy)-3-(S)-(4-fluoro)phenyl-4-(3-(5-oxo-1H,4H-1,2,4-triazolo)methylmorpholine having a particle size of less than 400 nm; about 5-15% by weight of a surface stabilizer; about 0-50% by weight of a redispersing agent; about 10-50% by weight of a solid support; and about 0-5% by weight of a lubricant.

9. A method for antagonizing the effect of substance P at its receptor site or for the blockade of neurokinin-1 receptors in a patient which comprises the administration to the patient of the composition of claim 1 in an amount that is effective for antagonizing the effect of substance P at its receptor site in the patient.

10. A method for treating emesis in a patient in need thereof which comprises administering to the patient an effective amount of the composition of claim 1.

\* \* \* \* \*